US008278031B2

(12) United States Patent
Pribenszky et al.

(10) Patent No.: US 8,278,031 B2
(45) Date of Patent: Oct. 2, 2012

(54) INCREASING THE VIABILITY OF MAMMALIAN OOCYTES

(75) Inventors: Csaba Pribenszky, Budapest (HU); Miklós Molnár, Budapest (HU); András Horváth, Üllö (HU)

(73) Assignee: Cryo Management Kft., Szombathely (HU)

( * ) Notice: Subject to any disclaimer, the term of this patent is extended or adjusted under 35 U.S.C. 154(b) by 1010 days.

(21) Appl. No.: 12/094,582

(22) PCT Filed: Nov. 21, 2006

(86) PCT No.: PCT/IB2006/054358
§ 371 (c)(1),
(2), (4) Date: Aug. 25, 2008

(87) PCT Pub. No.: WO2007/060608
PCT Pub. Date: May 31, 2007

(65) Prior Publication Data
US 2009/0017440 A1    Jan. 15, 2009

(30) Foreign Application Priority Data
Nov. 22, 2005   (HU) .................................... 0501079

(51) Int. Cl.
*A01N 1/00* (2006.01)
*A61B 17/43* (2006.01)
(52) U.S. Cl. .......................................... 435/1.1; 600/33
(58) Field of Classification Search .................. None
See application file for complete search history.

(56) References Cited

U.S. PATENT DOCUMENTS
7,879,539 B2    2/2011 Pribenszky et al.

FOREIGN PATENT DOCUMENTS
WO    2005/022996 A1    3/2005

OTHER PUBLICATIONS

Cryopreservation. Encyclopædia Britannica. Encyclopædia Britannica Online. Encyclopædia Britannica, 2011. Web. Jul. 20, 2011. <http://www.britannica.com/EBchecked/topic/1452607/cryopreservation>.*
Routray et al., "Factors affecting the uptake of DMSO by the eggs and embryos of medaka, Oryzias latipes", Theiogenology 58 : 1483-1496 (2002).*
Molnar et al., "Invenstigation on viability of embryos after exposing to high hydrostatic pressure", Theriogenology 57 : 506 (2002).*
Robertson "Assisted Reproductive Technology and the Family", Hastings Law Journal 47 : 911-933 (1995-1996).*
Arii et al., "Cryoprotection of Medaka embryos during development", Zoological Science 4 (5) : 813-818 (1987).
Welch et al., "Stress resopnse of *Escherichia coli* to elevated hydrostatic pressure", J Bacteriology, 1993, vol. 175, pp. 7170-7177.

Wemekamp-Kamphuis et al., "Enhanced levels of cold shock proteins in *Listeria monocytogens* L028 upon exposure to low temperature and high hydrostatic pressure", Applied and Environmental Microbiology, 2002, vol. 68, pp. 456-463.
Abe et al.: "Hydrostatic pressure promotes the acidification of vacuoles in *Saccharomyces cerevisiae*", FEMS Microbiol Lett, 1995, vol. 130, pp. 307-312.
Abe et al.: "Vacuolar acidification in *Saccharomyces cerevisiae* induced by elevated hydrostatic pressure is transient and is mediated by vacuolar H+-ATPase", Extremophiles,1997, vol. 1, pp. 89-93.
Abe et al.: Analysis of intracellular pH in the yeast *Saccharomyces cerevisiae* under elevated hydrostatic pressure: a study in baro-(piezo-) physiology. Extremophiles, 1998, vol. 2, pp. 223-228.
Abe et al.: "Pressure-regulated metabolism in microorganisms", Trends Microbiol, 1999, vol. 7, pp. 447-453.
Aldridge et al. "Pressure effects on mechanisms of charge transport across bilayer membranes", Biochim Biophys Acta, 1985, vol. 817, pp. 343-354.
Almlid et al.: "Effects of glycerol concentration, equilibration time and temperature of glycerol addition on post-thaw viability of boar spermatozoa frozen in straws", J. Anim. Sci.,1988, vol. 66, pp. 2899-2905.
Gill et al.: "Artificral insemination of beagle bitches with freshly collected, liquid stored, and frozen-stored semen", Am J Vet Res,1970, vol. 31, pp. 1807-1813.
Goodman et al.: "Retrospective evaluation of artificial insemination with chilled extended semen in the dog", J Reprod Fertil, 1993, vol. 47, p. 554. abstr.
Graumann et al.: "Cold shock proteins CspB and CspC are major stationary-phase-induced proteins in *Bacillus subtilis*", Arch Microbiol, 1999, vol. 171, pp. 135-138.
Gross et al.: "Proteins under pressure. The influence of high hydrostatic pressure on structure, function and assembly of proteins and protein complexes", Eur. J. Biochem., 1994, vol. 221, pp. 617-630.
Hackett et al.: "Reproductive performance of totally confined sheep bred with semen extended in a lactose-egg yolk-glycerol buffer and stored at 5 degrees C", Canadian Journal of Comparative Medicine. Revue Canadienne De Medecine Comparee, 1982, vol. 46, Issue 3, pp. 327-333.
Hancock et al.: "The collection of boar semen", Vet. Res.,1959, vol. 71, pp. 664-669.
Harrop: "Artificial insemination of a bitch with preserved semen", Br Vet J., 1954, vol. 110, pp. 424-425.
Ijaz et al. "Effect of various extenders and taunne on survival of stallion sperm cooled to 5 degrees C", Theriogenology, 1995, vol. 44, pp. 1039-1050.
Jaenicke: "Protein stability and molecular adaptation to extreme conditions", Eur J Biochem, 1991, vol. 202, pp. 715-728.
Johnson et al.: "The Cinetic Basis of Molecular Biology", Wiley, 1954, pp. 195-199.

(Continued)

Primary Examiner — Sandra Saucier
(74) Attorney, Agent, or Firm — Jason D. Voight

(57) ABSTRACT

The present invention relates to a method for improving viability and/or stress tolerance of viable biological material and using the said material comprising applying hydrostatic pressure to said biological material; keeping the said viable biological material at the hydrostatic pressure for a predetermined time period; releasing the hydrostatic pressure; and using the said material for any desired purpose in accordance with any useful protocol. The usage of the said biological material incorporates any techniques, protocols that are applicable in the field of assisted reproductive techniques, biotechnical and/or biotechnological manipulations.

15 Claims, No Drawings

OTHER PUBLICATIONS

Kaarniranta et al.: "Hsp70 accumulation in chondrocytic cells exposed to high continuous hydrostatic pressure coincides with mRNA stabilization rather than transcriptional activation", Proc. Natl. Acad. Sci. USA, 1998, vol. 95, pp. 2319-2324.

Katila et al.: "Comparison of three containers used for the tranSPOrt of cooled stallion semen", Theriogenology, 1997, vol. 48, pp. 1085-1092.

Latena et al.: "Identification of a cold-shock transcriptional enhancer of the Escherichia coli major cold shock gene encoding nucleotide protein H-NS", Proc. Natl. Acad. Sci. USA, 1991, vol. 88, pp. 10907-10911.

MacDonald: "The role of membrane fluidity in complex processes under high pressure", In: Jonnasch, H.W., Marquis, R.E., Zimmerman, A.M., editors, Current Perspectives in High Pressure Biology. London: Academic Press, 1987, pp. 207-223.

Maxwell et al.: "Membrane status of boar spermatozoa after cooling or cryopreservation", Theriogenology, 1997, vol. 48, pp. 209-219.

Murakami et al.: "DNA syntheseis in Tetrahymena: a pressure study", Cytobios, 1973, vol. 7, pp. 171-181.

O'Shea et al.: "Effects of Potassium on RAM Spermatozoa During Chilling to and Storage At 5 Degrees C", Journal of Reproduction and Fertility, 1964, vol. 53, pp. 121-132.

Palou et al.: "Kinetic analysis of Zygosaccharomyces bailii inactivation by high hydrostatic pressure", Lebensm.—Wiss. U. Technol., 1997, vol. 30, pp. 703-708.

Pequeux et al.: "Effects of high hydrostatic pressures on the activity of the membrane ATPases of some organs implicated in hydromineral regulation", Comp Biochem Physiol B Biochem Mol Biol, 1978, vol. 59, pp. 207-212.

Phadtare et al.: "Cold-shock response and cold-shock proteins", Curr Opin Microbiol, 1999, vol. 2, pp. 175-180.

Pinto et al.: "Fertility in bitches artificially inseminated with extended, chilled semen", Theriogenology, 1999, vol. 52, issue 4, pp. 609-616.

Pribenszky et al.: "Improving post-thaw survival of cryopreserved mouse blastocysts by hydrostatic pressure challenge", Anim. Reprod. Sci., 2005, vol. 87, pp. 143-150.

Pribenszky et al.: "Survival of mouse blastocysts after low temperature preservation under high pressure", Acta Vet. Hung., 2004, vol. 52, pp. 479-487.

Schmid et al.: "High pressure effects on the activity of glycolytic enzymes", Biophys Chem, 1975, vol. 3, ppl 90-98.

Schuster et al.: "The effect of hydrostatic pressure on S-layer-supported lipid membranes", Biochim Biophys Acta, 2002, vol. 1563, pp. 29-34.

Seki et al.: "Preserving tardigrades under pressure", Nature, 1998, vol. 395, pp. 853-854.

Silva et al.: "Pressure provides new insights into protein folding, dynamics and structure", Trends Biochem Sci, 2001, vol. 26, pp. 612-618.

Weber et al.: "The effect of high pressure upon proteins and other biomolecules", Q Rev Biophys, 1983, vol. 16, pp. 89-112.

Wouters et al.: "Analysis of the role of 7 kDa cold-shock proteins of Lactobacillus lactis MG1363 in cryoprotection", Microbiology, 1999, vol. 145, pp. 3185-3194.

Yager et al.: "Destabilization of a lipid non-bilayer phase by high pressure", Biochim Biophys Acta, 1983, vol. 731, pp. 491-494.

Yamanaka et al.: "The CspA family in Escherichia coli: multiple gene duplication for stress adaptation", Mol Microbiol, 1998, vol. 27, pp. 247-255.

Ferruzza et al.: "The Effect of Hydrostatic Pressure on the Development of Ascidian Eggs", Acta Embryologiae Experimentalis, 1979, issue 3, pp. 301-312.

Arai: "Effect of Allotriploidization on Development of the Hybrids between Female Chum Salmon and Male Brook Trout", Bulletin of the Japanese Society of Scientific Fisheries, 1986, vol. 52, pp. 823-829.

* cited by examiner

INCREASING THE VIABILITY OF MAMMALIAN OOCYTES

This is the National Stage of International Application PCT/IB2006/054358, filed Nov. 21, 2006.

The present invention relates to a method for improving viability and/or stress tolerance of viable biological material and using the said material comprising applying hydrostatic pressure to said biological material; keeping the said viable biological material at the hydrostatic pressure for a predetermined time period; releasing the hydrostatic pressure; and using the said material for any desired purpose in accordance with any useful protocol. The usage of the said biological material incorporates any techniques, protocols that are applicable in the field of assisted reproductive techniques, biotechnical and/or biotechnological manipulations.

BACKGROUND ART

The effect of hydrostatic pressure as a stressor in connection with increased stress tolerance and shock proteins has been studied in chondrocytes, yeast and bacteria, but not yet in gametes and embryos.

The physiological mechanisms by which microorganisms adapt to sublethal stresses are not yet understood well. Recent studies describe that instabilities caused by sublethal cold shock in the normal protein synthesis in bacteria are overcome by the synthesis of so-called cold-shock proteins (CSPs) (Phadtare et al., 1999). These CSPs are suspected to have many functions such as RNA chaperones (Graumann and Marahiel, 1999) or transcription activators (LaTena et al., 1991); it is assumed that they also play a role in the protection against freezing (Wouters et al., 1999). Further investigations found that the production of CSPs is induced not only by cold shock, but also by other environmental stresses. In *Escherichia coli*, for example, a type of CSP is produced by nutritional stress (Yamanaka et al., 1998).

Another trial showed that high hydrostatic pressure treatment provoked the production of certain cold-induced proteins and heat shock proteins (Welch et al., 1993). Since both cold shock and high pressure treatment increase CSP levels, trials were conducted about the possibility of cross-protection. Wemekamp-Kamphuis et al. (2002) found that the level of survival after pressurization of cold-shocked *Listeria monocytogenes* was 100-fold higher than that of the cells growing at 37° C.

Hydrostatic pressure in the range of 30-50 MPa usually inhibits the growth of various organisms: the initiation of DNA replication is one of the most pressure-sensitive intracellular processes (Abe et al., 1999). The effects vary in severity depending upon the magnitude and duration of compression (Murakami and Zimmerman, 1973). The cell membrane is noted as a primary site of pressure damage (Palou et al., 1997). High hydrostatic pressure treatment can alter the membrane functionality such as active transport or passive permeability and therefore may perturb the physico-chemical balance of the cell (Yager and Chang, 1983; Aldridge and Bruner, 1985; Macdonald, 1987; Schuster and Sleytr, 2002; Routray et al., 2002). The application of pressure can lead to changes in protein structure, including partially or completely unfolded conformations. Pressure can cause the denaturation of proteins (Schmid et al., 1975; Weber and Drickamer, 1983; Jaenicke, 1991; Gross and Jaenicke, 1994; Silva et al., 2001). Recent reports state that hydrostatic pressure enhances the production of shock proteins (Welch et al., 1993; Wemekamp-Kamphuis et al., 2002).

The physical or biochemical processes at altered pressure conditions are governed by the principle of Le Chatelier: all reactions that are accompanied by a volume decrease speed up considerably (Murakami and Zimmerman, 1973; Welch et al., 1993; Palou et al., 1997). The accumulation of the pressure effects is lethal beyond a certain level: while irreversible changes of some biomolecules take place at higher pressures, at 300 MPa most bacteria and multicellular organisms die. Though tardigrades—in their active state they die between 100 and 200 MPa—can survive up to 600 MPa if they are in a dehydrated state (Seki and Toyoshima, 1998). An early publication showed that biological systems are able to tolerate high pressures as long as the pressure is reduced slowly (Johnson et al., 1954). Pribenszky et al. (2003, 2004) also explored the possibility of gradual retrieval of the pressurized embryos and found that gradual release of pressure significantly improves survival.

In response to various stress stimuli, heat shock genes are induced to express heat shock proteins (HSPs). Previous studies have revealed that expression of heat shock genes is regulated both at transcriptional and posttranscriptional level, and the rapid transcriptional induction of heat shock genes involves activation of the specific transcription factor, heat shock factor 1 (HSF1). Furthermore, the transcriptional induction can vary in intensity and kinetics in a signal- and cell-type-dependent manner. Kaarniranta et al. (1998) demonstrated that mechanical loading in the form of hydrostatic pressure increases heat shock gene expression in human chondrocyte-like cells. The response to continuous HHP was characterized by elevated mRNA and protein levels of HSP70, without activation of HSF1 and transcriptional induction of hsp70 gene. The increased expression of HSP70 was mediated through stabilization of hsp70 mRNA molecules. Interestingly, in contrast to static pressurization, cyclic hydrostatic loading did not result in the induction of heat shock genes. The findings of Kaarniranta et al. (1998) showed that hsp70 gene expression is regulated post transcriptionally without transcriptional induction in chondrocyte-like cells upon exposure to high continuous hydrostatic pressure. They suggested that the posttranscriptional regulation in the form of hsp70 mRNA stabilization provides an additional mode of heat shock gene regulation that is likely to be of significant importance in certain forms of stress.

Previously, the present inventors found that a sublethal shock, high hydrostatic pressure (HHP), significantly improves the post-thaw survival of frozen mouse blastocysts (Pribenszky et al., 2005a, WO2005022996). Similarly, at semen cryopreservation, the average post-thaw motility was significantly superior with pressure pre-treatment in each of the pressurized bovine semen compared to the samples frozen without previous pressurization. The result clearly describes the beneficial effect of a previous pressure treatment to the post thaw motility of cryopreserved bull semen (Pribenszky et al., 2005b). Further investigations for exploring the biological background and biochemical change during the HHP process will unveil the mechanism of its protective effects. These studies, however, involve the cryopreservation of the biological material after the HHP pre-treatment, which is clearly not possible, or of low efficiency with a variety of biological material.

The process of semen chilling or storing at temperatures above 0° C. is well established to store spermatozoa for a short period of time [Hackett, et al., 1982; Pinto, 1999; O'Shea et al., 1964]. With optimal semen treatment (dilution) and storage at optimal temperatures the semen can be inseminated with acceptable fertility results (but with obviously reduced conception rates compared to fresh semen insemination) within 1-2 days post collection [Gill et al., 1970; Goodman and, Cain, 1993; Harrop, 1954; Ijaz and Ducharme, 1995; Katila et al., 1997] These methods follow very similar basic steps:
1. Semen collection.
2. Semen dilution at body temperature.
3. Optional centrifugation of the diluted semen. Re-extending the semen to adjust the optimal sperm-concentration.
4. Keeping the (re)extended semen at room temperature or 4-5° C. or any temperature that is above the freezing point of the sample.
5. Insemination of the semen.

Similarly to spermatozoa that suffer a loss of viability during storage, the survival capacity of embryos or oocytes also reduce once removed from their physiological maternal surrounding (for example for in vitro culture, activation, embryo transfer, splitting, sex determination, biopsy, in vitro maturation, ICSI, cloning or any type of biotechnological procedure). For this reason improving the viability/survival capacity of gametes and embryos before or after any procedure including from routine storage, insemination or transfer as far as the most complex biotechnological procedure is of great scientific and economic importance.

Similarly, for example during preservation of microorganisms, such as bacteria (e.g. freeze-drying), the viability of microorganisms is greatly compromised. Improving the efficacy of any process that comes together with improved viability bears immense scientific and economic significance.

As it is clear from the above, there is still a need in the art for the improvement of the viability of biological material that is widely used in biotechnology protocols.

The present inventors surprisingly found that by applying a hydrostatic pressure challenge the viability of biological materials can be improved significantly, and by the application of the method, many state of the art biotechnology protocols can be accomplished more efficiently. The present specification shows a wide range of examples on this finding: after applying the present method to embryo transfer or insemination, the conception rate and birth rate improved; by applying the present method to oocytes, their stress tolerance greatly increased, which resulted in improved cleavage rate and higher blastocyst formation rate; by applying the present method to semen, and then by following state of the art dilution and storage, the motility of the spermatozoa was preserved for a significantly longer period of time.

It was also surprising that the improvements were substantial even when avoiding to apply temperatures below the freezing point of the medium during any stage of the storage and/or manipulation of the biological material. This finding has significant practical implications for the usability of the present and similar HHP methods.

In this context we must emphasize that the present inventive concept equally applies to any different biotechnical/biotechnological protocol or procedure used in the assisted reproductive technologies (ART) and other procedures, and the choice of those is not limited with respect to the invention. The only necessary step to include in the improved protocols is the step of hydrostatic pressure challenge; the parameters of which can be easily optimized by a person skilled in the art when following the teachings of the present description.

Because semen freezing yields poor post-thaw survival of spermatozoa at boars (and horses as well), the most common tool of breeding at these species is the insemination of fresh, extended, extended and cooled or extended and chilled semen. By the use of HHP pre-treatment semen is significantly better preserved at the given temperature, and also, the time of storage with higher quality is considerably increased.

Similarly, in vitro and in vivo embryo production, in vitro culture of embryos, sexing, splitting, gene transfer, embryo transfer, oocyte maturation, activation, ICSI, cloning or any biotechnical/biotechnological procedure in the embryo, oocyte or sperm greatly reduce their viability/survival capacity. As an extrapolation of the above features, by the use of HHP pre-treatment gametes and embryos will enter any type of assisted reproductive technology (ART) or biotechnical/biotechnological procedure with an increased survival capacity.

DISCLOSURE OF INVENTION

Accordingly, the present invention relates to a method for improving viability and/or stress tolerance of viable biological material and using the said material comprising
(a) applying hydrostatic pressure to said viable biological material;
(b) keeping the said viable biological material at the hydrostatic pressure for a pre-determined time period;
(c) releasing the hydrostatic pressure;
(d) using the said material for any desired purpose in accordance with any useful protocol, with the proviso that the said usage does not comprise cryopreservation.

In an embodiment, pressure used in the method according to the invention is in the range of 1 to 200 MPa. In preferred embodiments, the pressure is preferably in the range of 10 to 100 MPa, more preferably 20 to 75 MPa, and most preferably 30 to 60 MPa.

In another embodiment, the hydrostatic pressure used in the method according to the invention is applied for a time period between 'instantaneous' and 300 minutes. In preferred embodiments, the pressure is applied preferably for a time period between 0.001 seconds and 600 minutes, preferably 1 seconds to 300 minutes, more preferably 10 seconds to 150 minutes, more preferably 20 seconds to 90 minutes, and most preferably 30 seconds to 60 minutes.

In other embodiments, the time period for releasing the pressure is between 10 sec and 2 hours, or between 1 min and 1 hour, or in other cases 10 min and 30 min. The release of pressure can be instantaneous.

In a preferred embodiment, the invention relates to a method where the pressure is applied, kept and released according to a predetermined pressure profile.

In another preferred embodiment, the invention relates to a method where the pressure is applied, kept and released according to a predetermined temperature profile.

In a preferred embodiment, the method according to the invention is used in connection with gametes and embryos selected from the group consisting of oocytes, sperms, zygotes, morulas, blastocysts, embryos, stem cells of a vertebrate animal.

Preferred embodiments relate to a method wherein the said vertebrate animal is a fish, bird or a mammal, preferably bovine, equine, caprine, ovine, swine, other livestocks, pets, primates, including human.

In another embodiment, the present invention relates to a method wherein the said biological material is a culture of micro-organisms.

In preferred embodiments of the present invention, the said culture of micro-organism is a bacterial culture.

The present invention further relates to any method as described above, wherein the usage of the said biological material incorporates any techniques, protocols that are applicable in the field of assisted reproductive techniques, biotechnical and/or biotechnological manipulations.

In a preferred embodiment, the protocol used in the method according to the present invention is freeze-drying.

In a further aspect, the method of the present invention applied to improve the stress tolerance of the viable biological material, wherein the tolerance against increased temperature is improved.

The present invention is described in more detail by using mouse embryos, bovine and boar spermatozoa, pig oocytes and two bacteria species for the purpose of demonstrating the inventive concept. It should be apparent that the disclosed procedures equally apply to all mammalian, avian or fish gametes and embryos, which are candidates of any kind of ART, or more generally, to any type of viable biological material usable in biotechnical or biotechnological procedures. For the sake of easy access and manipulation, mouse embryos, boar and bull semen, pig oocytes and two bacteria species were selected as the subjects of the detailed investigation. Also for the sake of easy interpretation and extrapolation, simple ART procedures were selected: embryo transfer, artificial insemination, oocytes in vitro activation and in vitro storage of semen. As far as the proof of concept experiment with micro-organisms is concerned, bacterium freeze-drying was selected to present the beneficial effect of high hydrostatic pressure pre/treatment. These procedures are the basic protocols of bacteriology, ART and related biotechnical or biotechnological procedures underlying their industrial, healthcare and research applicability. However, in the method according to the invention and similarly in the present description, the term 'mouse embryo' or 'bull or boar semen' can be used interchangeably with the term 'gamete or embryo'. For example, pre- and post-implantation stages of embryos, oocyte and sperm of vertebrate animals and human can be equally applied in the present method.

In the context of the present invention, the expression 'viable biological material' refers in general to a part of or originating from a living organism that has a capacity for living, developing, or germinating under favorable conditions. Without limitation, the viable biological material can be a cell, cell culture, tissue sample, tissue culture, organ, and the like.

With respect to micro-organisms, the term refers to an organism that is microscopic, i.e. too small to be visible to the naked eye. Micro-organisms can be bacteria, fungi, archaea or eukaryotes. Micro-organisms are often described as single-celled, or unicellular organisms; however, some unicellular protists are visible to the naked eye, and some multicellular species are microscopic.

As highly developed eukaryotic organisms, mouse embryos are more susceptible to the effect of hydrostatic pressure than tardigrades and bacteria. The first objective therefore is to establish the basic features of mouse embryos under pressure concerning their morphology and survival.

Carefully designed experiments were conducted to investigate the pressure tolerance of mouse embryos. The choice of pressure and time scale used was defined to give the widest applicable range for later practical applications. Therefore, the pressure for the use in the method according to invention is selected in the range from 1 MPa to 150 MPa. More particularly, the hydrostatic pressure that can be applied to the expanded blastocyst stage embryos is 1, 5, 10, 15, 20, 25, 30, 40, 50, 60, 70, 80, 90, 100, 110, 120, 130, 140 or 150 MPa, or any value in between these intermediate ranges. Similarly, a wide period of time can be selected for the mouse embryos to be kept under high hydrostatic pressure. More particularly, the mouse embryos are kept under the selected pressure for a time period between 1 sec. and 6 hours, more specifically 1 s, 5 s, 10 s, 20 s, 30 s, 40 s, 50 s, 1 min, 2 min, 3 min, 4 min, 5 min, 6 min, 8 min, 10 min, 15 min, 20 min, 30 min, 40 min, 50 min, 60 min, 70 min, 80 min, 90 min, 120 min, 150 min, 180 min, 210 min, 240 min, 300 min or 360 min. The time the embryos survive under pressure reduces with increasing pressure.

Embryos can survive a substantial amount of pressure without any visible change in their morphology (e.g., 90 MPa for 1 s or 30 MPa for 2 h). The embryos compacted depending on the magnitude and the duration of the applied pressure treatment. Without limiting the scope of the invention by theory, we assume that pressure can not be directly responsible for squeezing the water out of the blastocysts. Based on the cited documents, the compaction of the embryos was due to the consequences of pressure induced production of different proteins (cold-shock proteins, CSPs), reversible alterations in protein structure and metabolic processes. Compacted embryos could regain their normal morphology after 4-5 hours of in vitro culture, and resume development similarly to controls (e.g., embryos challenged by 90 MPa for 30 min or 30 MPa for 3 h).

Embryos from the above mentioned 'sublethal range' (e.g. compacted embryos) can preferably be selected for later transfer or any ART or biotechnological procedure. After pressurization, expanded blastocysts become compacted and stay in this form for 3-4 hours, then they re-expand. Based on this phenomenon, embryos treated with pressure before can be selected. Since the morphological changes of the embryos and the beneficial effects of the pressure pre-treatment may come from the altered protein structure and/or features and/or the enhanced production of different pressure-induced proteins, the examination of these proteins can be indicative of the high hydrostatic pressure applied to the biological material before any further process.

The higher the magnitude of the pressure, the less time the embryos survive. Pressure impact exceeding a certain magnitude and duration caused irreversible changes: embryos became disintegrated after 2 hours of in vitro culture or were already disintegrated after decompression (e.g., embryos challenged by 90 MPa for 2 h or 30 MPa for 5 h). The person skilled in the art should be capable of determine these limit-pressures and limit-times by routine experimentation with respect to the specific biological material used.

It will be appreciated that the survival rate of the pressurized embryos can be enhanced by gradual decompression thereof. Studies showed that the survival rate of the pressurized embryos increased strikingly if they were retrieved gradually. While 60 minutes at 90 MPa was lethal for all of the embryos, 80% survived when 120 min. gradual decompression was used. The decompression time is also a feature of the present invention which is up to the person skilled in the art to determine in view of the specific application. More particularly, the mouse embryos kept under the selected pressure are decompressed for a time period between 1 sec. and 4 hours, more specifically 1 s, 5 s, 10 s, 20 s, 30 s, 40 s, 50 s, 1 min, 2 min, 3 min, 4 min, 5 min, 6 min, 8 min, 10 min, 15 min, 20 min, 30 min, 40 min, 50 min, 60 min, 70 min, 80 min, 90 min, 120 min, 150 min, 180 min, 210 min or 240 min.

It will be appreciated by the person skilled in the art that the pressure treatment according to the present invention can be carried out according to any desired pressure profile. Therefore, the time dependence of the pressure as it applied, kept and released may vary according to different time—pressure curves, including all time point of the pressure treatment, i.e. during application of the pressure, during the course of the max pressure period, and during the pressure release phase. It is obvious that the pressure level at any given time point can be optimized and set according to easily performed preliminary experiments based on the present teaching without excess experimentation.

In another preferred embodiment, the method of the present invention can be carried out according to a predetermined temperature profile. The term 'temperature profile' refers to the time-temperature profile as it is measurable or set during the course of the pressure treatment, and it is independently controllable from the pressure applied. In preferred embodiments, the pressure treatment carried out at a single temperature, however, the biological material of interest may dictate the use of different temperatures at the different stages or parts of the stages of the pressure treatment. A set temperature may be any temperature, for example room temperature, ambient temperature, the native body temperature where the biological material is originating from, a temperature slightly elevated of the said native body temperature, and the like. The person skilled in the art can easily determine the applicability of any given temperature profile by analyzing the efficiency of the pressure treatment compared to a control experiment.

Without being limited by theory, a possible explanation of this feature could be that a considerable amount of $CO_2$ is generated under pressure (Abe and Horikoshi 1995). The hydration and ionization of $CO_2$ ($HCO_3^-$ and $H^+$) are facilitated by elevated pressure because the reaction is accompanied by a decrease in volume (−0.26 ml/mol) in a manner dependent on the magnitude of the pressure applied (Palou at al. 1997, Welch at al. 1993). The intracellularly produced carbon dioxide instantly dissolves, and then dissociates to give $HCO_3^-$ and $H^+$, thus also reducing the intracellular pH (Abe and Horikoshi 1995, 1997, 1998, Abe et al. 1999). It can be assumed that the equilibrium maintained by elevated pressure is lethal for the embryos at atmospheric pressure. It may be also hypothesized that the instant decrease of pressure causes elevated release of $CO_2$ from its hydrated and ionized form from the cytoplasm, causing immediate death of the embryos. On condition of a certain decompression time, the plasma membrane proteins ($H^+$-ATPase) (Schmid et al. 1975, Péqueux and Gilles 1978) reversibly inactivated by elevated hydrostatic pressure, start to function again, (together with passive diffusion) shifting the equilibrium gradually towards the physiological state.

After the treatment with carefully chosen pressurizing parameters, the embryos were cultured in vitro, then transferred into pseudopregnant mothers. The number of pups born after pressure-treatment of the embryos was higher than what was achievable without pressure treatment.

Similarly to the treatment of embryos, pig oocytes were also pressurized to examine their pressure-tolerance. Then, with carefully selected parameters, oocytes were pre-treated, stressed with an electric impulse 10 times greater than the optimal value, and were examined for cleavage and further development until the blastocyst stage. The number of in vitro activated oocytes that cleaved and developed further was higher with pressure-treatment than without.

Similarly to the treatment of embryos, bull and boar semen was also pressurized to examine the pressure-tolerance of spermatozoa. Then, with carefully selected parameters, semen was pre-treated, and kept in vitro at different temperatures. The number of motile spermatozoa in the different time points after semen collection was higher with pressure-treatment than without. The insemination of pressure treated boar semen yielded higher litter size than was achievable routinely in the facility.

Similarly to the above mentioned treatments, *Escherichia coli* and *Lactobacillus plantarum* samples were pressurized to examine if the survival of the bacteria can be increased after freeze-drying. The number of surviving bacteria in selected pressure/time parameters after freeze-drying was higher with pressure-treatment than without.

The present descriptions shows the improvement in the viability/survival capacity of biological material by hydrostatic pressure challenge using mouse blastocysts, pig oocytes, boar and bull spermatozoa and two bacterium species as model systems. This can be evaluated by transferring the pressurized embryos, following their treatment to culture medium and/or into pseudopregnant recipients; or in vitro activation; or inseminating the treated semen or counting the survival of bacteria after freeze-drying, respectively. In vitro development, implantation and further uterine development and cleavage and further development are obvious proofs of the embryos' and oocytes' viability. Similarly, the in vitro storage and insemination of the semen, yielding higher number of motile spermatozoa (in vitro) and higher pregnancy rates support the applicability of the said method.

The pressurization may be carried out by using any available pressurizing device that can be adapted to the protocols according to the present invention. Non-limiting examples of such instruments are for example the devices described in WO2005022996 or in the present document.

The present invention is further illustrated by the experimental examples described below, however, the scope of the invention will by no means be limited to the specific embodiments described in the examples.

EXAMPLE 1

Survival of Mouse Embryos at Different Pressures on Room Temperature, Effect of Pressure Treatment on Implantation and Birth Rates Embryo Production and Culture One-cell stage mouse embryos were collected from superovulated 6-8 week old CB6F1 donors and cultured at 37° C. with 5% $CO_2$ and maximal humidity in air in G 1.2 and G 2.2 mediums (Vitrolife, Göteborg) to the expanded blastocyst stage.

Pressurization

Blastocysts were loaded into 0.08 ml plastic straws (7-9 embryos/straw) with M2 (Sigma St. Louis, Mo.). Straws, filled with M2 as pressure medium, were placed into the chamber of a special custom-made device that is capable of generating and precisely detecting hydrostatic pressure up to 150 MPa. Achieving the desired amount of pressure took 20 seconds to 5 minutes (10 MPa to 150 MPa, respectively); the duration of releasing the pressure was 2-4 seconds.

Transfer

For in vivo evaluation, embryos pressurized with 600 bar for 30 min were cultured in G 2.2 for 2 hours as above. Then, they were transferred (7-12 embryos per animal) into Day 3 pseudopregnant recipients. Untreated blastocysts were transferred as controls.

Evaluation and Statistical Analysis

Conclusions were drawn from the changes in the morphological appearance of embryos examined at 400× magnification during 24 hours of continued in vitro culture, and from birth rate of the transferred embryos. Microscopically unchanged morphology of the blastomeres, reexpansion of the blastocoel and hatching from the zona pellucida were signs of in vitro survival. The number of fetuses at the 18 day dissection of the pregnant females or birth of healthy pups was proof of in vivo survival of the embryos. The survival rates were compared to control by chi-square test.

In the present experiments embryos were exposed to different hydrostatic pressures from 10 to 150 MPa (by 10 MPa increments) for various times, between 1 sec to 300 min, at room temperature.

The treatment exceeding a certain amount of pressure and time caused reversible morphological changes. The expanded blastocysts compacted inside the zona pellucida: the blastocoel disappeared, the size of the blastomers reduced but their structural integrity showed no alteration. After 4-5 hours of in vitro culture these blastocysts re-expanded and hatched from the zona pellucida in 24 hours (a). Embryos receiving less impact showed no morphological change and hatched within 24 hours of in vitro culture (b), while embryos challenged with a greater impact did not re-expand from the compacted stage and disintegrated within 2 hours, or were already disintegrated after decompression (c).

For in vivo evaluation, challenged embryos were judged 'survived' (a&b) and 'dead' (c) after 2 hours of in vitro culture after decompression and were transferred into recipients separately. Twenty nine pressure treated embryo were transferred to pseudopregnant mothers, out of which 28 were born. This ratio was higher then what was achievable with non-treated embryos. This significant improvement over the state of the art data (around 85%) also shows the robustness of the pressure pre-treatment. When the optimal pressure and time parameters are applied, the improvement of the viability of biological material still can be significant even when the baseline values quite high and already satisfactory for the industry. However, in the field of ART, every percentage point may have added economical significance.

EXAMPLE 2

Survival of Bull Spermatozoa at Different Pressures on Room Temperature, Effect of Pressure Treatment on the Prevention of the Decline of Sperm Motility Although bull semen is usually stored frozen, the feasibility of the present method was further tested in an industrially important system.

Semen of 13 bulls was diluted to a sperm concentration of $8 \times 10^7$/mL with AndroMed extender (MiniTüb, Tiefenbach, Germany). Diluted sperm was loaded into 0.25-mL straws at 25° C. Straws were divided into treatment groups and non-treated control group. The treatment groups were pressurized with computer controlled pressure machine (Cryo-Innovation, Budapest, Hungary) with 9 different profiles. For total/progressive motility testing CASA apparatus, SpermVision Version 3.0 (Minitüb, Tiefenbach, Germany) was used.

It was concluded that pressure-treatment below the 600 bar region does not affect negatively sperm survival. After 8 hours of semen storage at room temperature the motility of the treated/non treated samples were analysed again: the proportion of the motile cells were higher in the treated samples.

EXAMPLE 3

Survival of Boar Spermatozoa at Different Pressures on Room Temperature, Effect of Pressure Treatment on the Prevention of the Decline of Sperm Motility To further examine the applicability the method according to the invention, survival of boar spermatozoa was examined, where storage on room temperature is rather an industry standard.

Semen Collection

Semen was collected from boars twice a week. The filtered sperm-rich fraction was collected by gloved-hand technique into a 250-ml insulated vacuum bottle, then sperm was evaluated (Hancock and Hovell, 1959). The sperm-rich fractions of ejaculates with greater than 70% motile sperm were used.

Preparation of Semen

Frozen semen preparation followed a method previously described (Almlid and Johnson, 1988; Maxwell and Johnson, 1997) with a minor modifications. Briefly, the semen was diluted 1:2 with 37° C. Beltsville Thawing Solution (BTS) extender in the insulated bottle then was cooled at room temperature (20-23° C.) for 1 h after collection. After cooling, semen was transferred into 10 ml tubes, centrifuged at room temperature for 3 min at 2400× g, and the supernatant solution was discarded. The pellets were resuspended in lactose and egg yolk diluent at room temperature. Then glycerol diluent (the second diluent) and Equex paste (Minitüb, Tiefenbach, Germany) was added to the semen to give a final concentration of 6% glycerol and 0.5% Equex. Ministraws, 0.25 ml, (IMV, L'Aigle, France) were then filled with semen, straws were heat sealed. The concentration was set to provide $300 \times 10^6$ sperm/ml.

Pressurization

The straws were placed into the pressure chamber, filled with water as a pressure medium, of the pressurizing device, and the pre-determined pressure-protocol was applied. The custom-made pressurizing device was capable of providing precisely controlled pressure in the range of 10-1000 bars. It was made of stainless steel (KO 33) with the inner diameter of 20×220 mm, and was connected to a pressure gauge. A piston, moving in the pressure chamber generated the hydrostatic pressure. Speed of pressurization and depressurization was 200 bar/min.

Samples were pressurized at room temperature (RT) with either 200, 400 or 800 bars for either 40, 80 or 120 minutes. Non-pressurized samples were kept at room temperature for the corresponding time.

Evaluation

After 20 min incubation, two 5 µl drops were transferred onto glass slides and two 22 mm×22 mm cover-slips were applied. The samples were inserted in the microscope (Olympus BX 30), equipped with a 37° C. microscope stage and phase contrast optics (20X, Olympus, Japan) and 5-5 fields were evaluated from each drop by means of CASA apparatus, SpermVision Version 3.0 (Minitüb, Tiefenbach, Germany). Spermatozoa with VSL>10 µm/s and AOC>10 were considered progressive motile.

Results

After analyzing the motility parameters using mixed model (factors: time, pressure, date (random)), the pressure factor proved to be significant (p=0.001, total motility; p=0.0103, progressive motility). After multiple comparisons of the pressure treatments, the 800 bar treatment impact proved to be significantly (P<0.001, total motility; P<0.05, progressive motility) worse than the other levels (Table 1).

TABLE 1

Motility parameters (mean motility (std error)) following different pressure treatments

|  | 40 min | | 80 min | | 120 min | |
| --- | --- | --- | --- | --- | --- | --- |
|  | tm | pm | tm | pm | tm | pm |
| 200 bar | 81 (4) | 71.5 (6.5) | 91 (2) | 61 (16) | 82.5 (0.5) | 64 (16) |
| 400 bar | 87 (3) | 73 (2) | 87 (2) | 52 (9) | 80 (4) | 63 (9) |
| 800 bar | 65.5 (6.5) | 48 (2) | 78.5 (3.5) | 53.5 (9.5) | 69.5 (3.5) | 52 (10) |
| Atmospheric pressure | 88 (2) | 70 (11) | 88 (1) | 61 (10) | 80 (1) | 68.5 (8.5) | tm: total motility;
pm: progressive motility. There were 2 repetitions of each treatment combination.

Next, it was examined whether the application of pressure treatment affects the sperm motility rates after the 5 hours cold acclimatization time. A mixed model was fitted again with pressure, time and examination (with two levels: before and after the 5 hours acclimatization time), interactions of the fix factors, and date as random factor. Only the pressure and examination factors proved to be significant (Table 2).

TABLE 2

Motility parameters (mean motility (std error)) after 5 hours cold acclimatization time

|  | 40 min | | 80 min | | 120 min | |
| --- | --- | --- | --- | --- | --- | --- |
|  | tm | pm | tm | pm | tm | pm |
| 200 bar | 78.5 (1.66) | 51.25 (7.5) | 85.67 (2.33) | 71.33 (5.46) | 80 (2) | 56.5 (4.5) |
| 400 bar | 77 (1.58) | 63.25 (5.76) | 78.67 (4.18) | 64 (7.77) | 80.5 (4.5) | 74 (2) |
| 800 bar | 67 (4.53) | 46.75 (4.5) | 64 (0.58) | 47.33 (2.19) | 76.5 (1.5) | 66 (1) |
| Atmospheric pressure | 72.25 (2.56) | 47.75 (10.59) | 78.33 (4.1) | 60 (10.21) | 75 (4) | 45.5 (3.5) | tm: total motility;
pm: progressive motility. There were 4, 3 and 2 repetitions of each pressure treatments during 40, 80 and 120 minutes time intervals, respectively.

The total motility of the non-pressurized (atm) samples reduced significantly, while after the 200 and 400 bar treatments the motility did not reduce after 5 hours of cold acclimatization time, compared to the initial motility.

EXAMPLE 4

Effect of Pressure Treatment on the Fertilizing Capacity of Boar Spermatozoa

Five sows, already excluded from production, have been inseminated with pressure treated boar semen, in order to observe the fertilizing capacity of pressure treated spermatozoa, as well as to investigate any malformations in the offspring.

Ejaculates of two boars were extended 1:3 with commercial extender, at body temperature, then samples were let to cool down to room temperature in 30 minutes, before filling extended semen into infusion bags. Infusion bags were placed into the pressure chamber of an automatic pressurizing device (Cryo-Innovation Ltd., Budapest, Hungary) and pressure program was run at room temperature.

The pressure treatment used was 300 bars for 90 minutes. After treatment, semen samples were further extended with the same commercial extender at room temperature, then 5 sows were inseminated within 1 hour after pressurization.

Insemination was repeated 12 hours after the first insemination with the treated semen, left at 5° C. for the corresponding time.

At the ultrasound examination all the five saws were proved to be pregnant. Following normal delivery, 58 healthy piglets were born. The piglets were free from any defects and malformations.

It was concluded that the applied pressure treatment maintains the fertilizing capacity of boar spermatozoa, and does not cause any defect or malformation in the offspring. The average litter size in the farm was 9.8 piglets/sow, whereas with the applied pressure treatment resulted in 100% pregnancy rate and 11.6 average litter size. It was also concluded, therefore, that the applied pressure treatment increases the achievable average litter size, as well.

EXAMPLE 5

Survival (Cleavage Following In Vitro Activation) of Pig Oocytes after Different Pressure Treatments In vitro matured pig oocytes were activated via in vitro electro-activation following different pressure treatment combinations, in order to determine the pressure tolerance of the oocytes.

Six hundred in vitro matured, denudated oocytes were divided into treatment groups (n=15-20 oocytes/group) and control groups. Groups were pressurized in 0.5 ml artificial straws in TCM-HEPES medium (straws were sealed with mineral oil and metal ball) with 200-400 bar for 30-90 min at 24° C. and at 38.5° C. Controls were kept in the same circumstances, and one control group was left in the IVM medium in the thermostat for the corresponding time. After treatments, oocytes were activated in vitro, and placed into culture medium into 38.5° C. thermostat for further development. Cleavage was checked 48 hours after activation. Table 3 shows the percentage of oocytes in the different groups, that cleaved after in vitro activation.

TABLE 3

Percentage of oocytes cleaved after pressure treatments at 24° C. and at 38.5° C., 48 h after in vitro activation

| P | 30 min | 60 min | 90 min |
|---|---|---|---|
| (24° C.) | | | |
| 200 bar | 71% | 65% | 68% |
| 400 bar | 85% | 86% | 74% |
| Control group I.: | 65% | | |
| (38.5° C.) | | | |
| 200 bar | 91% | 94% | 76% |
| 400 bar | 72% | 75% | 83% |
| Control group II.: | 90% | | |
| Control group III. (thermostat): | 81% | | |

It was concluded that 200-400 bar treatments for 30-90 minutes were not harmful for the matured pig oocytes. Also, the 400 bar treatment for 30-60 minutes at 24° C., and the 200 bar treatment for 30-60 minutes at 38.5° C. yielded higher cleavage rates, than the corresponding control groups. Treatments were also made with 600-800 bar/30-90 minutes. In these groups no oocytes survived the treatments; these pressure parameters were detrimental.

EXAMPLE 6

Survival of In Vitro Matured Pig Oocytes after Different Pressure-Treatment Combinations, Activated with an Electric Pulse 10 Times Stronger than the Optimal In vitro matured pig oocytes were activated via 10× magnitude electro-activation in vitro, following different pressure treatment combinations, in order to examine, if treated oocytes better survive the detrimental electro-shock.

Three-six hundred in vitro matured oocytes (daily) were divided into treatment groups (n=15-20 oocytes/group) and control groups. Groups with cumulus cells were pressurized in 0.5 ml artificial straws in TCM-HEPES medium (straws were sealed with mineral oil and metal ball) with 200-800 bar for 30-120 min at 24° C. Controls were kept in the same circumstances, and one control group was left in the IVM medium in the thermostat for the corresponding time. After treatments, oocytes were denuded with vortexing, then activated in vitro with an electric impulse 10 times stronger than the optimal one, and then placed into culture medium into 38.5° C. thermostat for further development. Cleavage was checked 48 hours after activation, blastocyst formation was examined on the 6$^{th}$ day. Experiments were repeated 3 times.

TABLE 4

Percentage of the oocytes in the different groups, that cleaved and developed further after in vitro activation with 10x electric pulse.

| P | 30 min | 60 min | 120 min |
|---|---|---|---|
| 200 bar | 42% | 54% | 26% |
| 400 bar | 35% | 35% | 29% |
| 600 bar | 0% | 0% | 0% |
| 800 bar | 0% | 0% | |
| Control I. (24° C.): | 20% | | |
| Control II. (thermostat): | 10% | | |
| Blastocyst formation | | | |
| 200 bar | 47% | 44% | 32% |
| 400 bar | 29% | 35% | 28% |
| 600 bar | 0% | 0% | 0% |
| 800 bar | 0% | 0% | |
| Control I. (24° C.): | 28% | | |
| Control II. (thermostat): | 21% | | |

200-400 bar treatments for 30-60 minutes yielded significantly higher number of surviving oocytes than those without treatment or those treated with 600 or 800 bar. It was concluded that the 200 bar pressure treatments for 30 or 60 minutes proved to provide significantly superior cleavage rate and blastocyst rate compared to the control and other groups.

EXAMPLE 7

Survival of Bacteria after Different Pressure Treatment Combinations Followed by Freeze-Drying For the experiment two microbes, *Escherichia coli* and *Lactobacillus plantarum* were used. Cell counts were determined on TGE (Tripton Glucose Extract) nutritive media (MERCK) and MRS agar (MERCK), respectively. Cell counts were determined before preparing the treatment groups, after pressure treatments, and after 96 hours of incubation at 37° C. following freeze-drying (c.f.u.). Pressure treatments were executed with 9 pressurizing machines at the same time according to the following table:

| | Time | | |
|---|---|---|---|
| Pressure | 30 min | 60 min | 90 min |
| 200 bar | Treatment group 1 | Treatment group 2 | Treatment group 3 |
| 400 bar | Treatment group 4 | Treatment group 5 | Treatment group 6 |
| 600 bar | Treatment group 7 | Treatment group 8 | Treatment group 9 |

Samples were filled into 0.5 ml sterile artificial straws, and were sealed with sterile iron ball. Freeze-drying was made in Edwards freeze-drying equipment. Experiments were replicated two times. Results are presented in the following tables.

TABLE 5

Number of living *Lactobacillus plantarum* cells (c.f.u./0.4 ml) before and after freeze-drying (two repetitions). (Initial cell count (c.f.u./ml) before treatment: $9.0 \times 10^6 - 1.1 \times 10^7$)

| Treatment group No. | Before freeze-drying | After freeze-drying I. | After freeze-drying II. |
|---|---|---|---|
| 1 | $1.30 \times 10^7$ | $2.29 \times 10^6$ | $2.56 \times 10^6$ |
| 2 | $7.80 \times 10^6$ | $3.02 \times 10^6$ | $2.54 \times 10^6$ |
| 3 | $8.80 \times 10^6$ | $2.01 \times 10^6$ | $2.05 \times 10^6$ |
| 4 | $5.70 \times 10^6$ | $4.25 \times 10^6$ | $4.19 \times 10^6$ |
| 5 | $6.38 \times 10^6$ | $1.99 \times 10^6$ | $2.10 \times 10^6$ |
| 6 | $1.26 \times 10^7$ | $4.34 \times 10^6$ | $4.13 \times 10^6$ |
| 7 | $7.50 \times 10^6$ | $3.12 \times 10^6$ | $3.59 \times 10^6$ |
| 8 | $8.70 \times 10^6$ | $2.71 \times 10^6$ | $3.88 \times 10^6$ |
| 9 | $8.30 \times 10^6$ | $3.36 \times 10^6$ | $4.83 \times 10^6$ |
| Control | $1.05 \times 10^7$ | $2.56 \times 10^6$ | $4.08 \times 10^6$ |

TABLE 6

Number of living *Escherichia coli* cells (c.f.u./0.4 ml) before and after freeze-drying (two repetitions). (Initial cell count (c.f.u./ml) before treatment: $4.08 \times 10^8 - 4.10 \times 10^8$)

| Treatment group No. | Before freeze-drying | After freeze-drying I. | After freeze-drying II. |
|---|---|---|---|
| 1 | $6.10 \times 10^8$ | $1.55 \times 10^7$ | $1.65 \times 10^7$ |
| 2 | $3.20 \times 10^8$ | $2.56 \times 10^8$ | $2.90 \times 10^8$ |
| 3 | $4.80 \times 10^8$ | $9.30 \times 10^7$ | $9.0 \times 10^7$ |
| 4 | $3.90 \times 10^8$ | $1.36 \times 10^8$ | $1.00 \times 10^8$ |
| 5 | $5.90 \times 10^8$ | $2.14 \times 10^8$ | $1.80 \times 10^8$ |
| 6 | $5.95 \times 10^8$ | $2.27 \times 10^8$ | $1.70 \times 10^8$ |
| 7 | $6.10 \times 10^8$ | $7.50 \times 10^7$ | $9.50 \times 10^7$ |
| 8 | $6.60 \times 10^8$ | $1.65 \times 10^8$ | $7.80 \times 10^7$ |
| 9 | $6.20 \times 10^8$ | $1.52 \times 10^7$ | $1.21 \times 10^7$ |
| Control | $5.10 \times 10^8$ | $2.50 \times 10^7$ | $7.7 \times 10^7$ |

Treatment groups marked with bold numbers represent significantly higher cell survival rate compared to the control group. Amongst the treatment groups, groups No. 2 and No. 4 proved to be superior. It was concluded that a specific high hydrostatic pressure treatment before freeze-drying enhances significantly the cell survival rate after freeze-drying.

EXAMPLE 8

Survival of Bovine Embryos after Embryo-Biopsy or Sexing with/without Pressure Treatment Oocyte Collection and In Vitro Maturation (IVM)

COCs (aspirated from ovaries from slaughter house) are matured in TCM-199 Earl's supplemented with FCS, LH (Sigma), FSH (Sigma), L-Glutamine, penicillin and streptomycin, covered with mineral oil, in 38° C. with 5.1% $CO_2$ and maximal humidity in air for 22 hours.

Sperm Preparation, In Vitro Fertilization (IVF) and In Vitro Culture (IVC)

Fertilization medium is: TALP supplemented with BSA, penicilamin, hipotaurin, epinephrine and heparin covered with mineral oil.

Motile spermatozoa are obtained by centrifugation of frozen-thawed spermatozoa on a Percoll discontinuous density gradient (2 ml of 45% Percoll over 2 ml of 90% Percoll) for 20 min at 700 g at room temperature. After resuspension spermatozoa is added to the fertilization drops. Plates are incubated for 19 hr in 5% $CO_2$ in humidified air at 39° C. Presumptive zygotes are then cultured in vitro in SOF droplets under mineral oil in a humidified atmosphere of 5% $CO_2$ at 39° C.

Pressurization

Expanded blastocysts are loaded into 0.25 ml plastic straws without air-bubbles (7-9 embryos/straw), with embryo holding medium, then straws are sealed with PVC. Straws are placed into the pressurizing device (Cryo-Innovation Ltd., Budapest, Hungary). Embryos are exposed to different hydrostatic pressures from 60 to 90 MPa (by 10 MPa increments) for various times (15, 30, 45, 50, 60, 90, 100 minutes), at room temperature.

Results

The survival rate of the sexed embryos or embryos after biopsy is significantly higher with specially selected pressure treatment, than without.

EXAMPLE 9

Survival of Bovine Embryos after Gene Transfer with/without Pressure Treatment

In the present experiment bovine embryos are exposed to hydrostatic pressure in order to find out if their behavior under altered pressure conditions is similar to that of the mouse embryos. After challenging with hydrostatic pressure, samples are subjected to gene transfer. After in vitro culture and transfer, the survival of the samples is enhanced compared to the samples that were not treated with pressure previously.

EXAMPLE 10

Survival of Human Embryos after ICSI and Embryo Biopsy with/without Pressure Treatment In the present experiment bovine embryos are exposed to hydrostatic pressure in order to find out if their behavior under altered pressure conditions is similar to that of the mouse embryos. After challenging with hydrostatic pressure, samples are subjected to ICSI or biopsy. After in vitro culture and transfer, the survival of the samples is enhanced compared to the samples that were not treated with pressure previously.

EXAMPLE 11

Survival of Oocytes (Human, Bovine, Caprine, Swine) after Pressure Treatment, In Vitro Storage and Maturation The aim of the present experiment is to prove that oocytes tolerate any process (including in vitro storage/maturation) with a lot higher efficacy if they are treated previously with hydrostatic pressure. Oocytes are treated with hydrostatic pressure and samples are kept in vitro after releasing the pressure. The in vitro and in vivo survival of the oocytes is enhanced compared to the samples that were not treated with pressure previously.

EXAMPLE 12

Survival of Embryonic Stem Cells after Pressure Treatment, In Vitro Storage

The aim of the present experiment is to prove that the survival of embryonic stem cells is enhanced by a previous pressure treatment. Mouse embryonic stem cells are treated with hydrostatic pressure and samples are stored and treated after releasing the pressure. After the in vitro and in vivo survival of the cells is enhanced compared to the samples that were not treated with pressure previously.

The results presented in the present examples show that the pressure treatment applied prior to any type of assisted reproductive or biotechnological technique improves the survival (stress tolerance) of the gametes and embryos (and stem cells). Also, the presented data on mouse embryos, bull and boar spermatozoa, big oocytes and bacteria indicate the wide applicability of the inventive concept. The application of the method according to the present invention can be useful in improving success rates in all kind of assisted reproductive or biotechnological techniques, embryo-manipulation, including other mammalian species, humans not excluded. The present method also opens wide possibilities for other fields where manipulation of gametes and embryos can find its applications.

Because semen freezing yields poor post-thaw survival of spermatozoa at boars (and horses as well), the most common tool of breeding at these species is the insemination of fresh, extended, extended and cooled or extended and chilled semen. By the use of HHP pre-treatment semen is significantly better preserved at the given temperature, and also, the time of storage with higher quality is considerably increased.

Similarly, in vitro and in vivo embryo production, in vitro culture of embryos, sexing, splitting and using any biotechnical/biotechnological procedure, embryo transfer, oocyte maturation, ICSI or any biotechnical/biotechnological procedure in the oocyte or sperm greatly reduce their viability/survival capacity. As an extrapolation of the above features, by the use of HHP pre-treatment gametes and embryos will enter any type of assisted reproductive technology (ART) or biotechnical/biotechnological procedure with an increased survival capacity. [C1]

REFERENCES

Abe, F., and Horikoshi, K. (1995). Hydrostatic pressure promotes the acidification of vacuoles in *Saccharomyces cerevisiae*. FEMS Microbiol Lett 130, 307-312.

Abe, F., and Horikoshi, K. (1997). Vacuolar acidification in *Saccharomyces cerevisiae* induced by elevated hydrostatic pressure is transient and is mediated by vacuolar H+-ATPase. Extremophiles 1, 89-93.

Abe, F., and Horikoshi, K. (1998). Analysis of intracellular pH in the yeast *Saccharomyces cerevisiae* under elevated hydrostatic pressure: a study in baro- (piezo-) physiology. Extremophiles 2, 223-228.

Abe, F., Kato, C., and Horikoshi, K. (1999). Pressure-regulated metabolism in microorganisms. Trends Microbiol 7, 447-453.

Aldridge, B. E., Bruner, L. J. (1985). Pressure effects on mechanisms of charge transport across bilayer membranes. Biochim Biophys Acta 817, 343-354.

Almlid T., and Johnson L. A., 1988. Effects of glycerol concentration, equilibration time and temperature of glycerol addition on post-thaw viability of boar spermatozoa frozen in straws. J. Anim. Sci. 66:2899-2905.

Gill H P, Kaufman C F, Foote R H, Kirk R W. (1970) Artificral insemination of beagle bitches with freshly collected, liquid stored, and frozen-stored semen. Am J Vet Res 1970; 31:1807-1813.

Goodman M F, Cain Jt. (1993) Retrospective evaluation of artificial insemination wrth chilled extended semen in the dog. J Reprod Fertil 1993; 47:554. abstr.

Graumann, P. L., Marahiel M. A. (1999). Cold shock proteins CspB and CspC are major stationary-phase-induced proteins in *Bacillus subtilis*. Arch Microbiol 171, 135-138.

Gross M., and Jaenicke R., 1994. Proteins under pressure. The influence of high hydrostatic pressure on structure, function and assembly of proteins and protein complexes. Eur. J. Biochem. 221:617-630.

Hackett, A J; Wolynetz, M S (1982): Reproductive performance of totally confined sheep bred with semen extended in a lactose-egg yolk-glycerol buffer and stored at 5 degrees C Canadian Journal Of Comparative Medicine. Revue Canadienne De Medecine Comparee, Volume 46, Issue 3, July 1982, Pages 327-333

Hancock J. L., and Hovell G. L. R., 1959. The collection of boar semen. Vet. Res. 71:664-669.

Harrop A E. (1954) Artificial insemination of a bitch with preserved semen Br Vet J. 1954; 110:424-425.

Jaenicke, R. (1991). Protein stability and molecular adaptation to extreme conditions. Eur J Biochem 202, 715-728.

Johnson F. H., Eyring H., Polissar M. J., 1954. The Cinetic Basis of Molecular Biology. Wiley, New York.

Kaarniranta K., Elo M., Sironen R., Lammi M. J., Goldring M. B., Eriksson J. E., Sistonen L., and Helminen H. J., 1998. Hsp70 accumulation in chondrocytic cells exposed to high continuous hydrostatic pressure coincides with mRNA stabilization rather than transcriptional activation. Proc. Natl. Acad. Sci. USA 95: 2319-2324.

Katila T, Combes G B, Varner D D, Blanchard T L (1997) Comparison of three containers used for the tranSPOrt of cooled stallion semen. Theriogenology 1997; 48: 1085-1092.

LaTena A., Brandi A., Falconi M., Spurio R., Pon C. L., and Gualerzi C. O., 1991. Identification of a cold-shock transcriptional enhancer of the *Escherichia coli* major cold shock gene encoding nucleotide protein H-NS. Proc. Natl. Acad. Sci. USA 88, 10907-10911.

Ijaz A, Ducharme R.(1995) Effect of various extenders and taunne on survival of stallion sperm cooled to 5'° C. Theriogenology 1995, 44: 1039-1050.

Macdonald, A. G. (1987). The role of membrane fluidity in complex processes under high pressure. In: Jonnasch, H. W., Marquis, R. E., Zimmerman, A. M., editors. Current Perspectives in High Pressure Biology. London: Academic Press pp. 207-223.

Maxwell W. M. C., and Johnson L. A., 1997. Membrane status of boar spermatozoa after cooling or cryopreservation. Theriogenology 48:209-219.

Murakami, T. H., Zimmerman, A. M. (1973). DNA syntheseis in Tetrahymena: a pressure study. Cytobios 7, 171-181.

O'SHEA, T; WALES, R G (1964): EFFECTS OF POTASSIUM ON RAM SPERMATOZOA DURING CHILLING TO AND STORAGE AT 5 DEGREES C. Journal Of Reproduction And Fertility, Volume 53, August 1964, Pages 121-132.

Palou, E., Lopez-Malo, A., Barbosa-Canovas, G. V., Welti-Chanes, J., and Swanson, B. G. (1997). Kinetic analysis of *Zygosaccharomyces bailii* inactivation by high hydrostatic pressure. Lebensm.-Wiss. U. Technol. 30, 703-708.

Péqueux, A., and Gilles, R. (1978). Effects of high hydrostatic pressures on the activity of the membrane ATPases of some organs implicated in hydromineral regulation. Comp Biochem Physiol B Biochem Mol Biol 59, 207-212.

Phadtare, S., Alasina, J., Inouye, M. (1999). Cold-shock response and cold-shock proteins. Curr Opin Microbiol 2, 175-180.

Pinto, C R; Paccamonti, D L; Eilts, B E (1999) Fertility in bitches artificially inseminated with extended, chilled semen. Theriogenology, Volume 52, Issue 4, September 1999, Pages 609-616;

Pribenszky C., Molnar M., Cseh S., Solti L., 2005a. Improving post-thaw survival of cryopreserved mouse blastocysts by hydrostatic pressure challenge. Anim. Reprod. Sci. 87. 143-150.

Pribenszky C., Molnar M., Solti L., Dengg J., Lederer J., 2005b. The effect of high hydrostatic pressure on the motility of fresh and frozen-thawed bull semen (pilot study). Reproduction in domestic animals 40. 338.

Pribenszky Cs., Molnar M., Cseh S., and Solti L., 2003. Viability of embryos after exposing to high hydrostatic pressure. Theriogenology 59, 329 (Abstract).

Pribenszky Cs., Molnar M., Cseh S., and Solti L., 2004. Survival of mouse blastocysts after low temperature preservation under high pressure. Acta Vet. Hung. 52, 479-487.

Routray R., Suzuki T., Strussmann C. A., Takai R., 2002. Factors effecting the uptake of DMSO by the eggs and embryos of medaka, *Oryzias latipes*. Theriogenology 58:1483-1496.

Schmid, G., Lüdemann, H. D., and Jaenicke, R. (1975) High pressure effects on the activity of glycolytic enzymes. Biophys Chem 3, 90-98.

Schuster, B., Sleytr, U. B. (2002). The effect of hydrostatic pressure on S-layer-supported lipid membranes. Biochim Biophys Acta 1563, 29-34.

Silva, J. L., Foguel, D., Royer, C. A. (2001). Pressure provides new insights into protein folding, dynamics and structure. Trends Biochem Sci 26, 612-618.

Weber, G., Drickamer, H. G. (1983). The effect of high pressure upon proteins and other biomolecules. Q Rev Biophys 16, 89-112.

Welch, T. J., Farewell, A., Neidhardt, F. C., Bartlett, D. H. (1993). Stress response of *Escherichia coli* to elevated hydrostatic pressure. J Bacteriol 175, 7170-7177.

Wemekamp-Kamphuis, H. H., Karatzas, A. K., Wouters, J. A., Abee, T. (2002). Enhanced levels of cold shock proteins in *Listeria monocytogenes* LO28 upon exposure to low temperature and high hydrostatic pressure. Appl Environ Microbiol 68, 456-63.

Wouters, J. A., Jeynov, B., Rombouts, F. M., de Vos, W. M., Kuipers, O. P., Abee, T. (1999). Analysis of the role of 7 kDa cold-shock proteins of *Lactobacillus lactis* MG1363 in cryoprotection. Microbiology 145, 3185-3194.

Yager, P., Chang, E. L. (1983). Destabilization of a lipid non-bilayer phase by high pressure. Biochim Biophys Acta 731, 491-494.

Yamanaka, K., Fang, L., Inouye, M. (1998). The CspA family in *Escherichia coli*: multiple gene duplication for stress adaptation. Mol Microbiol 27, 247-255.

The invention claimed is:

1. A method for improving the viability of a viable biological material and using the material comprising:
   (a) applying hydrostatic pressure to said biological material;
   (b) keeping said viable biological material at the hydrostatic pressure for a predetermined time period;
   (c) releasing the hydrostatic pressure;
   (d) using the viable biological material in the field of assisted reproductive techniques,
   with the proviso that no cryopreservation of the viable biological material is performed, and wherein the viable biological material is an oocyte of a mammal.

2. The method according to claim 1 wherein said hydrostatic pressure is in the range of 1 to 200 MPa.

3. The method according to claim 2 wherein said hydrostatic pressure is applied for a time period between 10 seconds and 150 minutes.

4. The method according to claim 1 wherein said hydrostatic pressure is applied for a time period between 0.001 seconds and 600 minutes.

5. The method according to claim 4 wherein said hydrostatic pressure is in the range of 10 to 100 MPa.

6. The method according to claim 1 wherein said pressure is released gradually over a time period between instantaneous release and 6 hours.

7. The method according to claim 1 wherein said pressure is applied, kept and released according to a predetermined pressure profile.

8. The method according to claim 1 wherein said mammal is selected from the group consisting of bovine, equine, caprine, ovine, swine, other livestocks, pets, and primates.

9. The method according to claim 1 wherein said hydrostatic pressure is in the range of 10 to 100 MPa.

10. The method according to claim 1 wherein said hydrostatic pressure is in the range of 20 to 75 MPa.

11. The method according to claim 1 wherein said hydrostatic pressure is in the range of 30 to 60 MPa.

12. The method according to claim 1 wherein said hydrostatic pressure is applied for a time period between 1 second and 300 minutes.

13. The method according to claim 1 wherein said hydrostatic pressure is applied for a time period between 10 seconds and 150 minutes.

14. The method according to claim 1 wherein said hydrostatic pressure is applied for a time period between 20 seconds and 90 minutes.

15. The method according to claim 1 wherein said hydrostatic pressure is applied for a time period between 30 seconds and 60 minutes.

* * * * *